(12) United States Patent
Maresky et al.

(10) Patent No.: US 10,729,389 B2
(45) Date of Patent: Aug. 4, 2020

(54) 3D ASSESSMENT OF CONJUGANT EYE DEVIATION FOR THE IDENTIFICAITON OF ACUTE ISCHEMIC STROKE

(71) Applicants: Hillel Sarel Maresky, Toronto (CA); Miriam Michelle Klar, Bergenfield, NJ (US); Sigal Tal, Savyon (IL); Max Levitt, Toronto (CA)

(72) Inventors: Hillel Sarel Maresky, Toronto (CA); Miriam Michelle Klar, Bergenfield, NJ (US); Sigal Tal, Savyon (IL); Max Levitt, Toronto (CA)

(73) Assignee: Hillel Sarel Maresky, Toronto (CA)

(*) Notice: Subject to any disclaimer, the term of this patent is extended or adjusted under 35 U.S.C. 154(b) by 127 days.

(21) Appl. No.: 16/201,136

(22) Filed: Nov. 27, 2018

(65) Prior Publication Data

US 2019/0192089 A1   Jun. 27, 2019

Related U.S. Application Data

(60) Provisional application No. 62/591,348, filed on Nov. 28, 2017.

(51) Int. Cl.
| | |
|---|---|
| *A61B 6/03* | (2006.01) |
| *A61B 5/00* | (2006.01) |
| *A61B 6/00* | (2006.01) |
| *G06T 7/00* | (2017.01) |
| *A61B 8/13* | (2006.01) |

(52) U.S. Cl.
CPC ........... *A61B 6/032* (2013.01); *A61B 5/0042* (2013.01); *A61B 6/501* (2013.01); *A61B 6/504* (2013.01); *A61B 6/507* (2013.01); *A61B 6/5217* (2013.01); *G06T 7/0012* (2013.01); *A61B 5/0035* (2013.01); *A61B 8/13* (2013.01); *G06T 2207/10081* (2013.01); *G06T 2207/30016* (2013.01)

(58) Field of Classification Search
CPC ....... A61B 6/032; A61B 5/0042; A61B 6/501; A61B 8/13; A61B 5/0035; G06T 7/0012
See application file for complete search history.

(56) References Cited

U.S. PATENT DOCUMENTS

| | | | | |
|---|---|---|---|---|
| 2006/0110008 | A1* | 5/2006 | Vertegaal | G06T 7/251 382/103 |
| 2011/0194745 | A1* | 8/2011 | Dafni | A61B 6/032 382/131 |
| 2012/0155731 | A1* | 6/2012 | Weersink | G06T 7/344 382/131 |

(Continued)

OTHER PUBLICATIONS

Prevost MJL, Deviation des yeux et de la tete dans quelques cas d'hemiplegie. Gazette Hebdomadaire de Medecine et de Chirurgie 1865;41:649-650.

(Continued)

*Primary Examiner* — Congvan Tran
(74) *Attorney, Agent, or Firm* — Katten Muchin Rosenman LLP

(57) ABSTRACT

Disclosed herein are systems and methods for computing a 3D conjugate gaze adjusted length (CGAL) using 3D scans. The measurements for determining CGAL are measured on a clipping plane generated from the 3D CT scans. Acute ischemic strokes (AIS) is determined if the CGAL is greater than 0.28 with high specificity.

9 Claims, 9 Drawing Sheets

(56) References Cited

U.S. PATENT DOCUMENTS

| | | | |
|---|---|---|---|
| 2015/0288944 A1* | 10/2015 | Nistico | G06T 15/20 345/156 |
| 2016/0210503 A1* | 7/2016 | Yin | G06K 9/00335 |
| 2020/0020098 A1* | 1/2020 | Odry | G06K 9/6244 |
| 2020/0090334 A1* | 3/2020 | Sheth | A61B 6/507 |
| 2020/0113462 A1* | 4/2020 | Mart Nez Pineiro | A61B 5/04001 |

OTHER PUBLICATIONS

S. Payabvash, et al., Clinical implications of eye deviation on admission CT examination of acute ischaemic stroke patients, Clinical Radiology 71 (2016) 1314e11-1314e15.

Shoichiro Sato, et al., Conjugate Eye De-viation in Acute Intracerebral Hemorrhage: Stroke Acute Management With Urgent Risk-Factor Assessment and Improvement-ICH (SAMURAI-ICH) Study, Stroke. 2012;43(11):2898-2903.

Oliver C. Singer, et al., Conjugate eye deviation in acute stroke: inci-dence, hemispheric asymmetry, and lesion pattern, Stroke 2006;37:2726-2732.

D. McKean, et al., Validating a threshold of ocular gaze deviation for the prediction of acute ischaemic stroke, Clinical Radiology 69 (2014), 1244-1248.

Roger E. Kelley, et al., Horizontal gaze paresis in hemispheric stroke, Stroke 17(5) Jan. 1986,1030-1032.

Kara M Schwrta, et al., Frequency of eye deviation in stroke and non-stroke patients undergoing head CT, Neurocrit Care 2012;17:45-48.

Clarity R. Coffman, et al., The "DeyeCOM Sign": predictive value in acute stroke code evaluations, Journal of Stroke and Cerebrovascular Diseases 2015;24:1299-1304.

Nirav H Shah, MD, et al., Conjugate Eye Deviation on CT Associated With Worse Outcomes Despite IV Thrombolysis, Neurohospitalist 2017;7(2):74-77.

Cees C. Tijssen, MD, et al., Prognostic significance of conjugate eye deviation in stroke patients, Stroke 1991;22:200-202.

Ennio De Renzi, MD, et al., Conjugate gaze paresis in stroke patients with unilateral damage. An unexpected instance of hemispheric asymmetry, Arch Neurol 1982;39:482-486.

Chin-Sang Chung, et al., Striatocapsular haemorrhage, Brain 2000;123:1850-1862.

Chin-Sang Chung, et al., Thalamic haemorrhage, Brain 1996;119:1873-1886.

WS Lesley, et al., Predicting acute ischaemic stroke by measuring the degree of ocular gaze deviation (Prevost's sign) on CT, J Neurointerv Surg 2009;1:32-34.

Elisabeth Becker, et al., Neuroimaging of eye position reveals spatial neglect, Brain 2010;133:909-914.

J.E. Simon, et al., CT assessment of conjugate eye deviation in acute stroke, Neurology 2004;62:523-524.

M Fruhmann Berger, et al. , Deviation of eyes and head in acute cerebral stroke, BMC Neurol 2006;6:23, pp. 1-8.

K.J.M. Frusch, et al., Association between eye position on brain scan and hospital mortality in acute intracerebral hemorrhage, Eu-ropean Journal of Neurology. 2016;23(4):831-835.

Hans-Otto Karnath, et al., The subcortical anatomy of human spatial ne-glect: putamen, caudate nucleus and pulvinar, Brain 2002;125:350-360.

Hideaki Tanaka, MD, et al., Conjugate eye deviation with head version due to a cortical infarction of the frontal eye field, Stroke. 2002;33(2):642-643.

V. Mahajan, et al., Eye position information on CT increases the identification of acute ischaemic hypoattenuation, AJNR Am J Neuroradiol 2008;29:1144-1146.

H. Maresky, et al., Revisiting the Prevost Sign: Assessment of Conjugate Gaze in Acute Stroke Imaging Using 3-Dimensional Multi-Detector Computed Tomography (MDCT) Post-Processing Soft-ware, Innovation and informatics poster presentation at: Radiological Society of North America Annual Meeting; Nov. 29, 2016; Chicago, IL, USA, 65 sheets.

Michael P. Marks, et al., Evaluation of Early Computed Tomographic Findings in Acute Ischemic Stroke, Stroke. Jan. 1999;30(2):389-392.

T. Moulin, MD., et al., Early CT signs in acute middle cerebral ar-tery infarction: Predictive value for subsequent infarct locations and outcome, Neurolo-gy. 1996;47(2):366-375. doi:10.1212/wnl. 47.2.366.

Mannudeep K. Kalra, MD, et al., Strategies for CT radiation dose optimization, Radiology. 2004;230(3):619-628.

Jeffrey L. Saver, MD, et al., Time Is Brain—Quantified, Stroke. Aug. 2005;37(1):263-266.

* cited by examiner

3D ASSESSMENT OF CONJUGANT EYE DEVIATION FOR THE IDENTIFICAITON OF ACUTE ISCHEMIC STROKE

CROSS-REFERENCE TO RELATED APPLICATION

The present application claims priority to U.S. Provisional Application Ser. No. 62/591,348, filed Nov. 28, 2017, the entire contents of which are hereby incorporated by reference in their entirety.

FIELD OF THE INVENTION

The present invention relates to identifying acute ischemic strokes (AIS) using 3D computed tomography (CT) scans. More particularly, the present invention discloses a system and method for identifying AIS by computing a 3D conjugate gaze adjusted length (CGAL) using 3D CT scans.

BACKGROUND

Conjugative shift of horizontal gaze towards the affected hemisphere is a well-recognized occurrence in AIS patients, as first described by Jean Louis Prevost in 1865. Commonly referred to as conjugate eye deviation (CED), it is often assessed in clinical stroke severity diagnostic tools such as the National Institute of Health Stroke Scale/Score (NIHSS).

CED appears in more than 55% of the computerized tomography (CT) scans taken upon hospital admission in AIS patients. Moreover, studies evaluating the clinical significance of CED in AIS patients have repeatedly demonstrated that the degree of deviation is associated with stroke severity at hospital intake and poor prognostic outcomes, with the direction of deviation typically presenting ipsilateral to the affected brain hemisphere. CED-causing lesions in AIS patients generally reflect damage to cortical areas involved in the control of spatial attention, eye movements, and the frontal eye fields. These findings suggest that CED identification may be a useful tool in the assessment of AIS severity and infarction location, as well as prognostic outcome.

There has previously been no clear consensus on the threshold at which CED is thought to become a significant observation, but is has been noted a high specificity (95.9%) for a CED of >11.95° on CT imaging following acute infarct. Despite being highly specific, only a 17% sensitivity has been noted. This in turn means an 83% false negative rate, representing a failure to detect the majority of AIS cases based on this criteria. Thus, while this threshold may be a helpful additional tool in the detection of acute infarct, its clinical utility remains to be improved.

Additionally, it appears that that the utility in identifying CED is negated in patients with large hypoattenuation, as is often the case in patients with a CED of >11.95°. Specifically, past research has demonstrated that CED recognition on CT scan does not increase reader identification of acute ischemic hypoattenuation if four or more Alberta Stroke Program early CT score (ASPECTS) zones are involved. Similarly, NIHSS and CED degree are linked such that a patient with a CED of >11.95° will likely present with a wealth of other identifiable symptoms, which further decreases the unique contribution of CED in AIS diagnosis. Taken together, this research suggests that CED identification at the currently established threshold may not be a useful tool in the diagnosis of AIS.

As noted, CED's strong association with AIS gives it potential as a useful diagnostic tool. Nonetheless, prior research has also demonstrated the limitations of CED as it stands, which emphasizes the importance of improvements to the tool. Accordingly, there exists a need for an improved system and method for increasing the efficacy of CED as a tool for the identification of AIS.

SUMMARY

To identify AIS according to the present invention, a CD scan of the patient's brain is first performed to acquire axial CT image slices. 2D lateral deviation is then calculated using the image slices. If the measured CED is greater than >11.95°, 3D lateral deviation is then calculated. Otherwise, if the CED is less than <11.95°, further measurements are not calculated.

Next, a 3D volume rendered model of the patient's brain is constructed from the axial CT image slices. The resulting 3D model is clipped coronally and tangentially to the frontal bone until the lens, roof of the orbit, and the zygomatic arch are exposed. A snapshot of the aligned 3D model is then acquired.

The process of acquiring the aligned snapshot can be performed manually by a technician or completely automated. For example, a convoluted neural network (CNN) may be trained with a plurality of CT (or other neurodiagnostic imaging) scans in which the clipping of the scan has been correctly performed (training dataset). The CNN can then be used to automatically acquire the snapshot.

CED measurements, taken from the snapshot, are adjusted to account for variation in patients' globe size. To do so, the vector length from the center of the lens to the center of the globe is measured. The vector angle is then calculated according to an azimuth algorithm in which the object of interest is placed on a 360° plane to allow for description of the vector angle. Angles between 0-180° are designated as positive, indicating a rightward directed gaze, and angles between 180°-360° are designated as negative, indicating a leftward directed gaze.

Globe radius of the eye is then measured. The vector length is then divided by the globe radius, producing a size-adjusted measurement that referred to herein as the Conjugate Gaze Adjusted Length (CGAL). As will be described later, it was determined that CGAL was heavily correlated with NIHSS. A CGAL >0.25, >0.27 and >0.35 exhibited a specificity of 66%, 89% and 89% and a sensitivity of 91%, 86% and 82% respectively in the identification of AIS.

DETAILED DESCRIPTION

Figure 1:
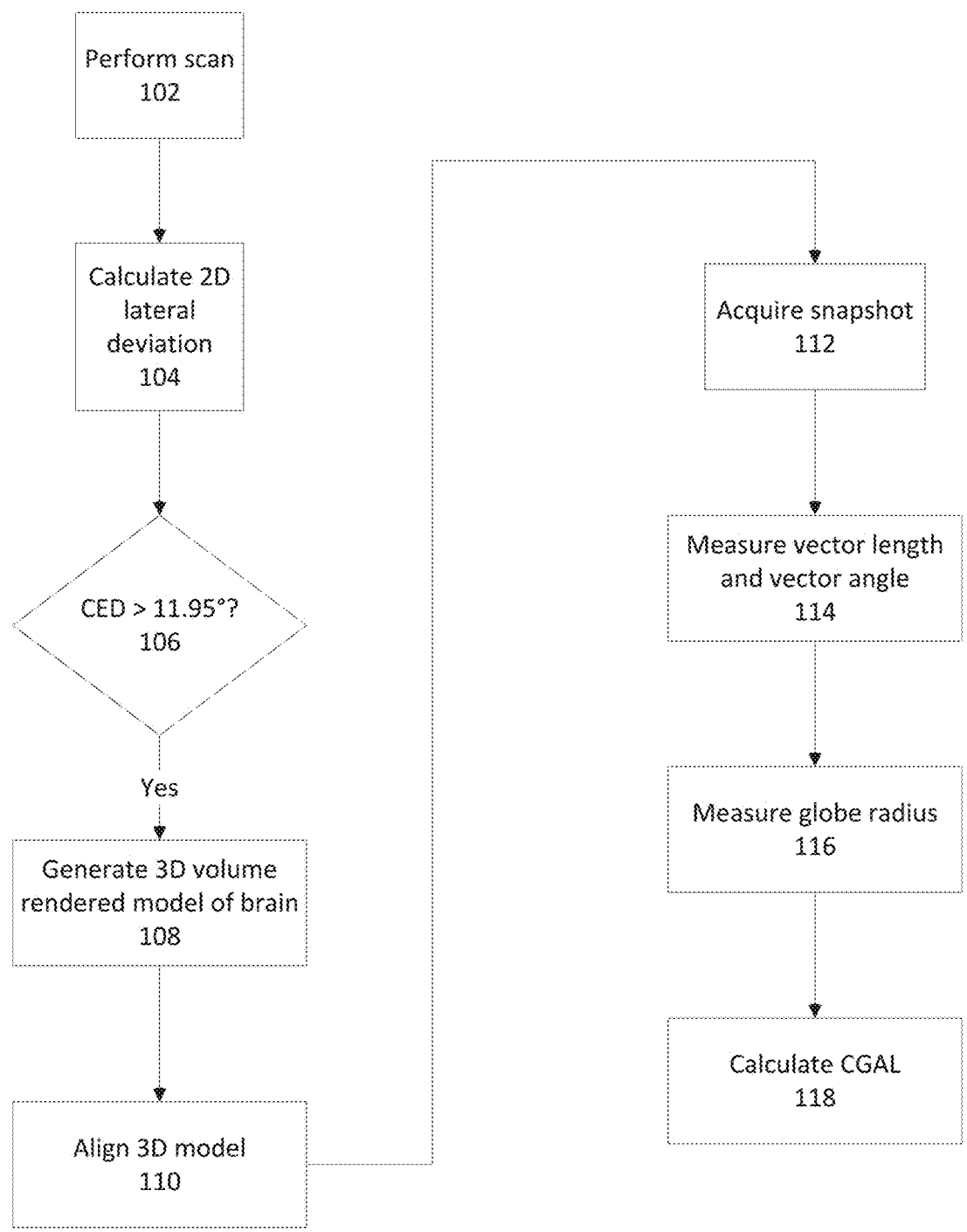
FIG. 1 depicts a flowchart showing the steps utilized to calculate CGAL.

Referring first to FIG. 1, depicted is a flowchart showing the steps utilized to calculate CGAL according to the present invention. In step 102, a CT scan of a patient is first performed in step 102. The CT scan provides the necessary information for determining CGAL and its usefulness in the identification of AIS.

The CT scan (and any follow-up scan) is preferably performed with identical, standard non-contrast CT protocol. In some embodiments, the CT scanner is Philips Brilliance 64 MDCT machine (kVP 120, mAs 400 with dose modulation, FOV 225 mm axial slice thickness 3 mm, coronal and sagittal slice thickness 0.50 mm). The CT suite and procedure used in the present study had no features that would lead participants to direct their gazes toward any particular direction.

Alternatively, MRI scans using coronal or 3D sequences or even 3D sonography may be used for acquiring such procurements.

Figure 2:
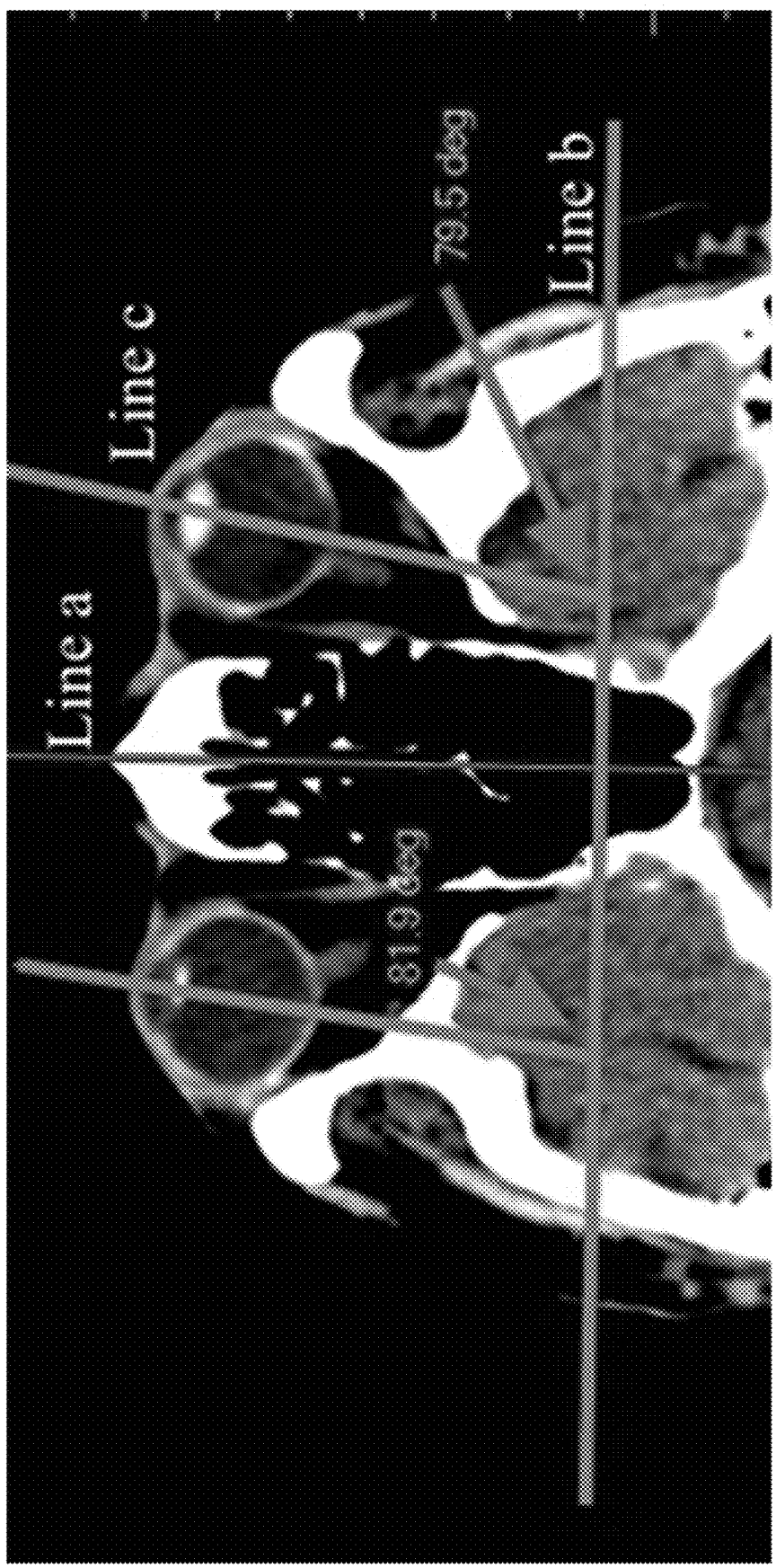
FIG. 2 depicts a sample CT image slice and the calculated 2D lateral deviation.

In step 104, 2D lateral deviation is then calculated from one of the CT image slices. Preferably, a 2D axial view produced using Philips Intelspace software is used to generate the CT image slice used in step 104. For illustration, FIG. 2 depicts a sample CT image slice and the calculated 2D lateral deviation. In order to measure the eye deviation, three lines are fitted to the CT image slice. A first line is fitted anteroposteriorly through the cranium at the midline (line a). The second line (line b) is drawn perpendicular to line a. A final set of lines, line c, are drawn through each lens of the eye at the long axis (line c). The eye deviation for both the right (OD) and left (OS) eye is then measured by the angle found at the intersection of lines b and c.

In the depicted example of FIG. 2, the CEDs are 8.1° and 10.5°. According to the determination made in step 106, in which the CED is compared to the 11.5° threshold for CED, it would be determined that the patient imaged in FIG. 2 is not a suitable candidate for the calculation of CGAL and the process would terminate. However, if it is determined that the measured 2D lateral deviation is greater than 11.5°, a 3D volume rendered model of the patient's brain is generated in step 108. Software, such as Philips Intellispace Portal, is used to generate the 3D volume rendered model using a "soft tissue" window. The Phillips Intelspace software processes the CT scan information from step 102 and provides the viewer with an option on how to view the CT scan. Preferably, a 3D reconstruction, which is a standard function in the software, is used.

Figure 3B:
FIG. 3B depicts a top cross-section image slice from a CT scan.
Figure 3A:
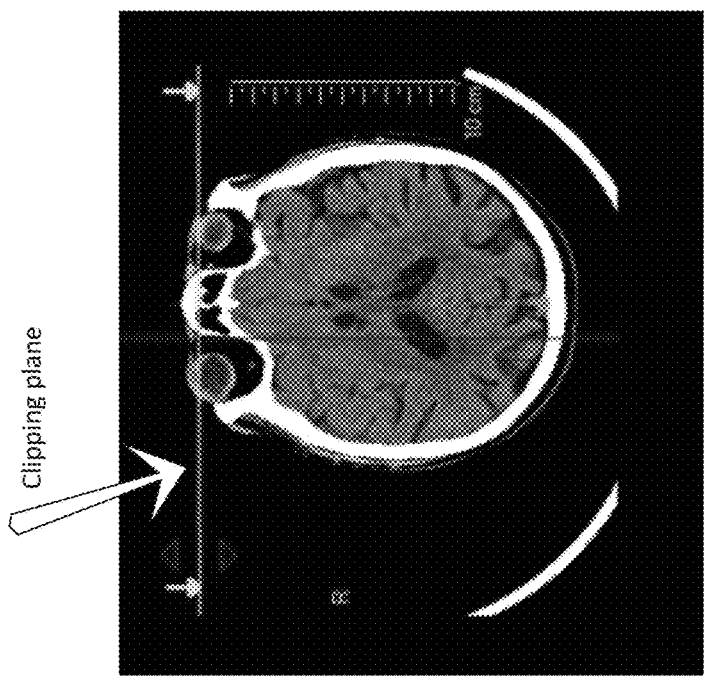
FIG. 3A depicts a side cross-sectional image slice from a CT scan.
Figure 3C:
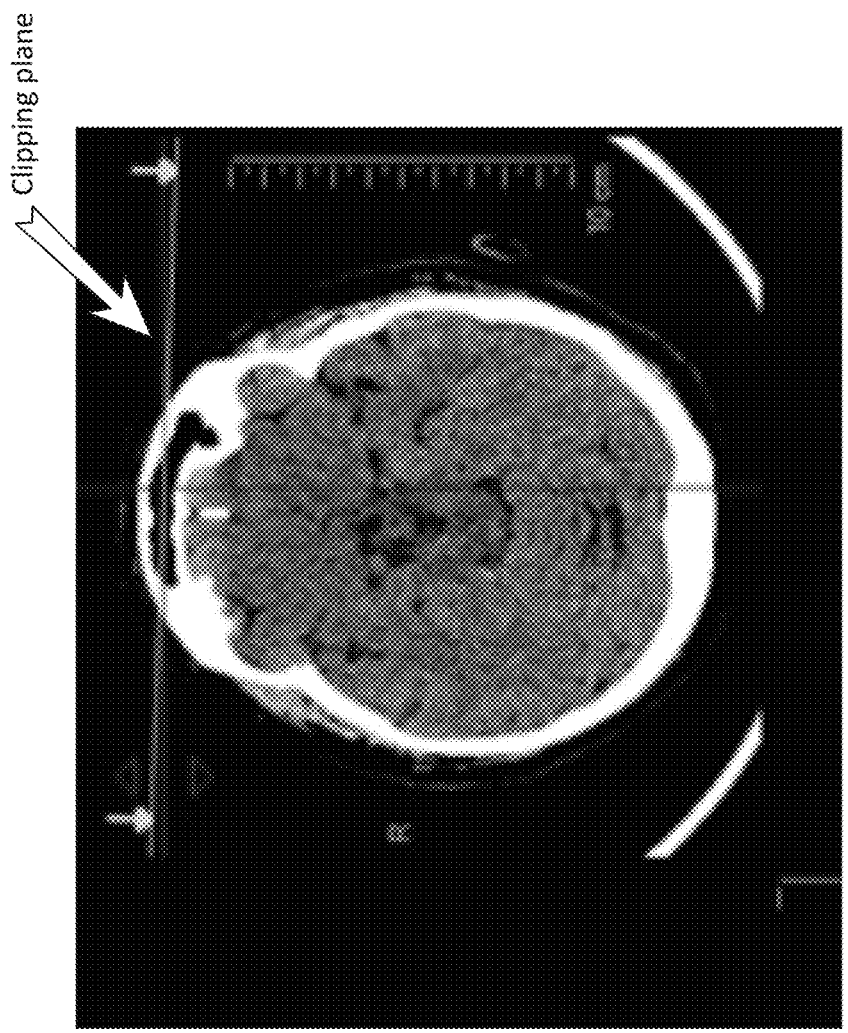
FIG. 3C depicts a bottom cross-section image slice from a CT scan.

A clipping plane of the 3D volume rendered model is then determine in step 110. The clipping plane is determined by tilting the regular coronal orthogonal 90° plane and fitting that coronal plane to a virtual line connecting the frontal bone to the zygoma in the sagittal plane. It is important to note that each patient has his/her own unique clipping plane according to the facial structure of the frontal bone and zygoma. As an example, FIGS. 3A-3C depict top, side, and bottom cross-sectional slices, respectively, showing the final location of the coronal plane A in the 3D volume rendered model after fitting has been performed. The clipping plane clips coronally and tangentially to the frontal bone until the lens, roof of the orbit, and zygomatic arch are exposed. In order to ensure proper alignment, the clipping plane can be scrolled in the anterior-posterior direction until the globe and lens are both contained in the clipping plane.

Figure 4:
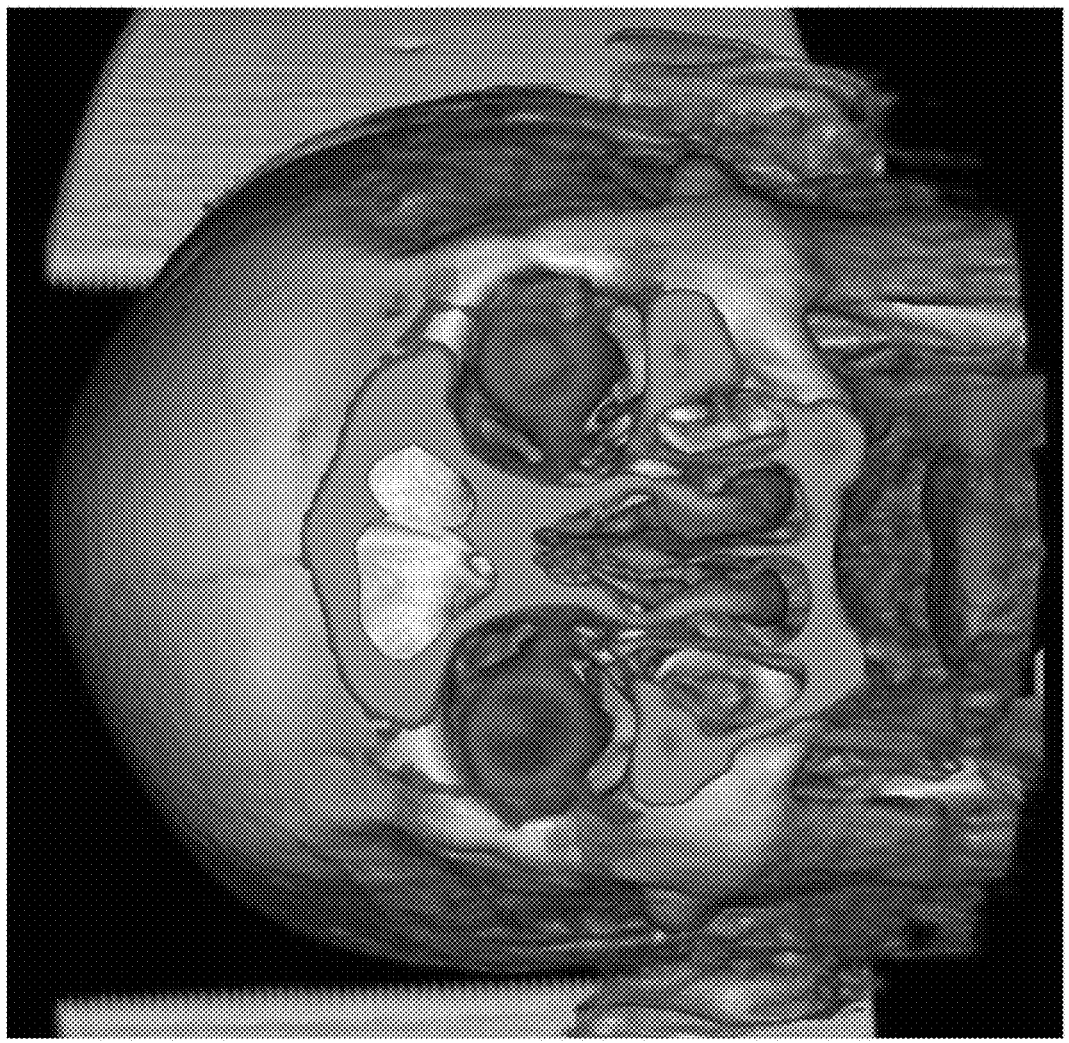
FIG. 4 depicts a snapshot from the CT scan taken at the clipping plane.

Using the clipping plane, a front view (3D coronal/oblique plane) "snapshot" including the patient's eyes is generated in step 112. An example of the front view snapshot produced from the clipping plane of FIGS. 3A-3C is depicted in FIG. 4. From this image, CGAL is determined.

Figure 5:
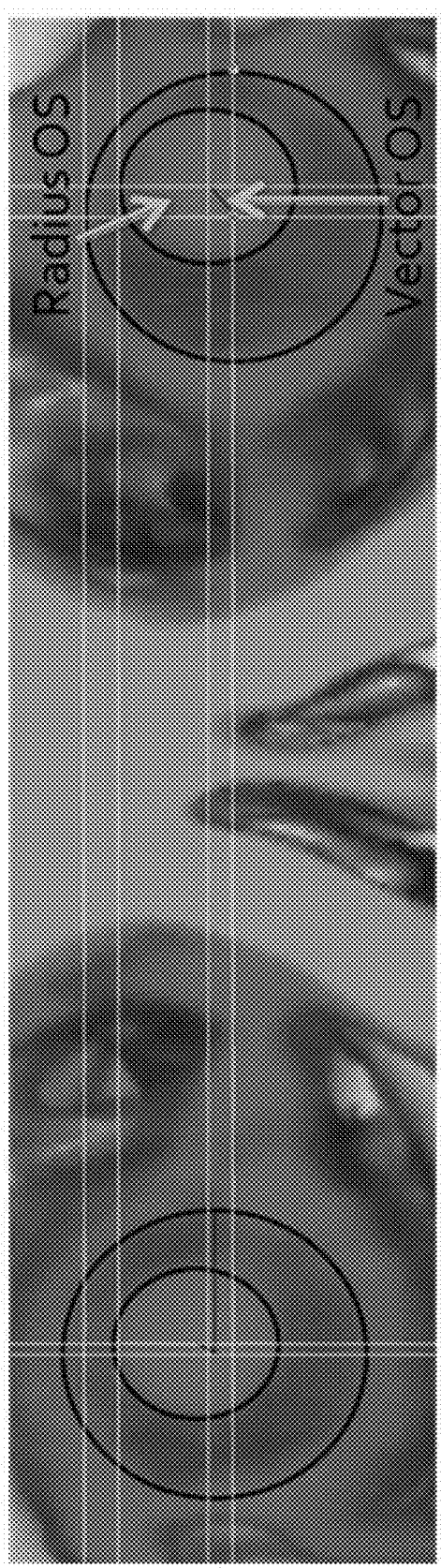
FIG. 5 depicts the identification of the vector length and vector angle from the snapshot.

Next, the deviation of each eye is measured in the snapshot by measuring the vector length and vector angle of each eye in step 114. This process can be performed manually, using commercial software such as Adobe Photoshop, or can be automated by using a CNN to identify the vector length and vector angle for each eye (i.e., from a vetted initial training set). An example of how this step is performed is depicted in FIG. 5. As shown, crosshairs are fitted to the center of the globe of each eye (the expected center) and a vector is fitted from the center of the globe (outer highlighted perimeter) to the center of the lens (inner highlighted perimeter). This specifies the length and angle of the vector for each eye.

Figure 6:
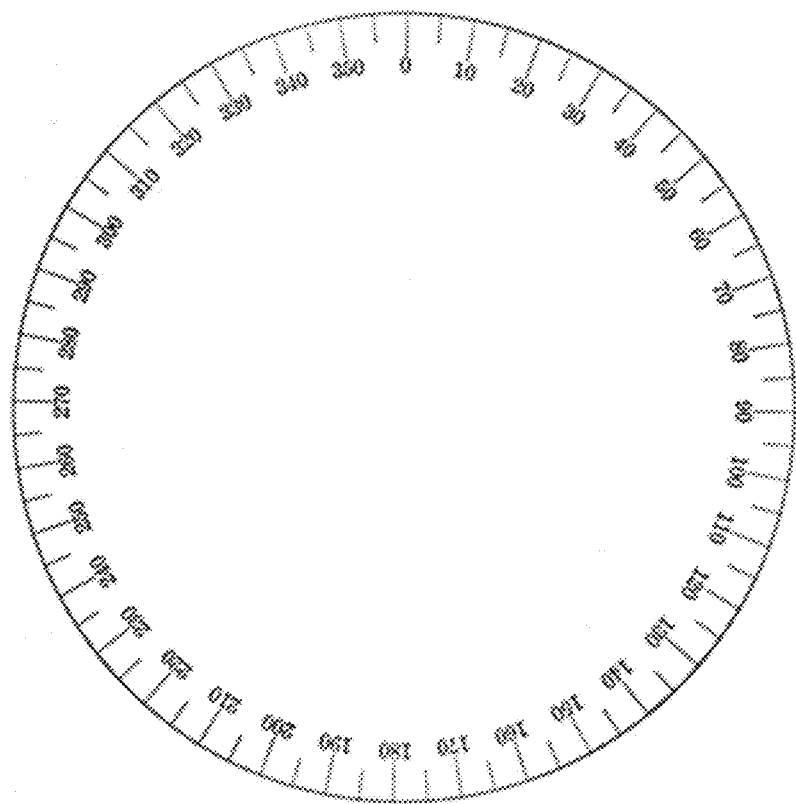
FIG. 6 depicts a virtual 360° plane that is created around each eye to calculate the vector angle.

The direction of deviation (vector angle) is calculated using a four quarter azimuth algorithm. As depicted in FIG. 6, a virtual 360° plane is created around each eye with the center of the globe of each eye being the center of the 360° plane. From this diagram and the calculated vector, the angle of the vector is specified. Angles between 0°-180° are designated as positive, indicating a rightward directed gaze, and angles be-tween 180°-360° are designated as negative, indicating a leftward directed gaze.

Using the snapshot, the globe radius of each eye is then measured in step 116. This can be calculated for each eye by measuring the distance from the center of the fitted crosshairs through the globe to the outer highlighted perimeter which represents the bounds of the globe of each eye.

From the vector length calculated in step 114 and the globe radius measured in step 116, the CGAL of each eye can be calculated in step 118 by dividing the vector length by the globe radius. The CGAL homogenizes results, as different people have a different sized and shape globes and true Globe radius does change (from person to person) while the amount of deviation forces the clipping plane to a slightly different radius (i.e. the more deviation, the seemingly smaller the globe, because of the lens's proximity to the perimeter).

Specifically, a machine learning algorithm, such as Amazon Rekognition, can be automatically used to identify (a) the lens and its center (inner highlighted perimeter) (b) the perimeter of the globe (outer highlighted perimeter), and (c) the expected location lens (i.e., the center of the globe identified by the crosshairs). The algorithm (e.g., using Python) can then calculate the distance between the expected center and the location of the lens center (calculated in step 114) and divide this number by the radius of the globe (calculated in step 116) to determine CGAL (step 118).

In the example depicted in FIG. 5, Vector OS is the calculated vector and Radius OS is the calculated radius of the lens. This leads to a CGAL of 0.3 cm which is obtained by dividing Vector OS by Radius OS (04 cm/1.2 cm) and the vector angle is 45°. Using this algorithm, the deviation angle and CGAL for each eye can be accurately calculated.

All of the calculations and 3D modeling described with respect to steps 104-118 of FIG. 1 can be completely automated using a computer. As previously mentioned, a CNN can be trained to automatically identify features from the CT scan such as the globe and lens of the eye. The alignment of the 3D model at the clipping plane can also be automated by training a computer (e.g., using machine learning techniques) to ensure that all of the required elements are included in the final slice image.

CGAL essentially more effectively measures the true deviation of each eye. The globe of each eye is a fixed size (determined by the bones forming it). In a healthy individual, the lens is located in the center of the globe. Therefore, measuring the distance from the center of the globe to the center of the lens will give a constant measurement, X. However, in the case of a stroke, where there is eye deviation, the center of the lens to the center of the globe measurement will no longer be X because of the eye deviation. The eye deviates away from the center of the orbit, which brings the lens closer to the perimeter (wall of the orbit/globe). And, as previously explained, the deviation of each eye can occur in any of three dimensions and cannot accurately be perceived using only 2D CT data. The calculation of CGAL using the snapshot allows for a more accurate quantification of the amount of CED for each individual compared to prior art methods.

In order to verify that CGAL is a useful tool for diagnosing AIS, and to determine an acceptable useful clinical value for CGAL, a retrospective analysis of 519 patients who had CT scans for suspected cerebrovascular accidents (CVA) within 20 minutes of hospital admission was performed. Direction and angle of eye deviation were calculated based on 2D axial images. Exclusion criteria included patients for whom CVA was identified as a transient ischemic attack, non-ischemic intracranial disease was identified, CT scans could not be 3D reconstructed due to excessive patient motion during the scan, patients who had previously undergone ocular lens surgery, patients who previously underwent enucleation of one or two eyes, patients under the age of 18, pregnancy, or patients lacking signatory capacity.

When available, follow up CT and magnetic resonance imaging (MRI) scans, taken between one to fourteen days after patient intake, were obtained for diagnosis confirmation. In the analysis, the follow up MRI scans were performed using standard diffusion-weighted imaging (DWI) protocol on either Siemens Magnetom Aera 1.5 T or Siemens Magnetom Skyra 3 T MR imaging machines. The CT suite and procedure used in the analysis had no features that would lead participants to direct their gaze toward any particular direction. The absence of features was particularly important because it could affect results by altering the gaze of participants.

Figure 8:
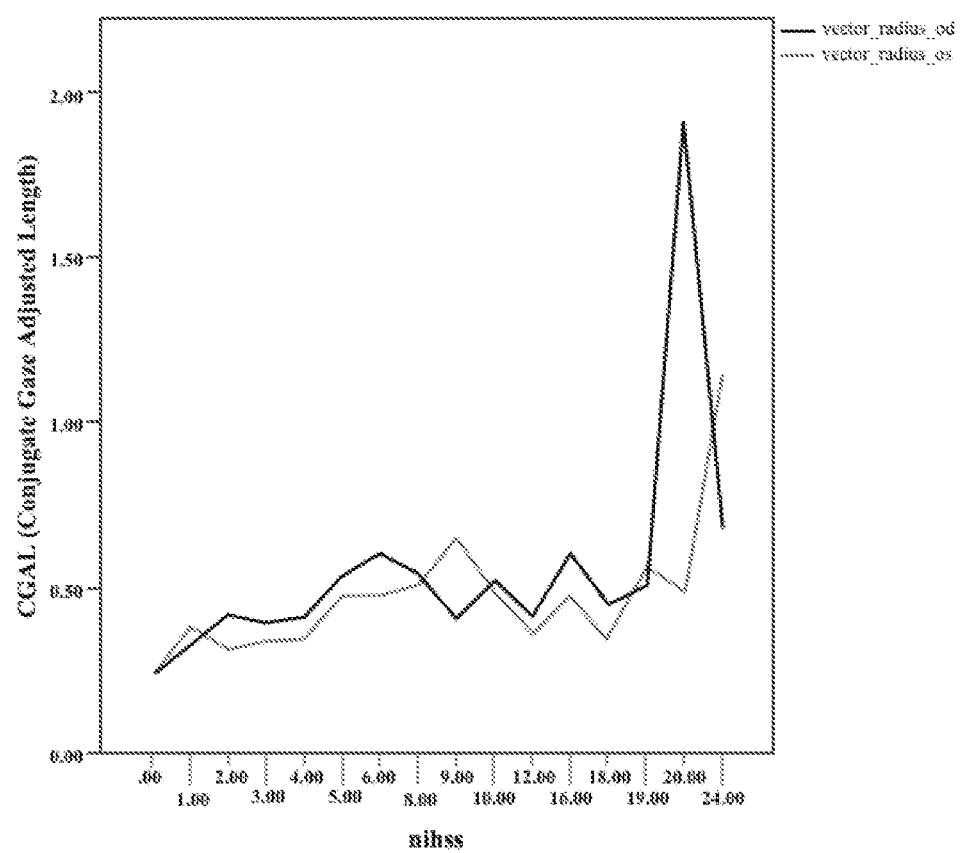
FIG. 8 depicts a chart showing correlation between CGAL deviation values and NIHSS score.

Statistical analyses were performed using IBM Statistical Package for the Social Sciences (SPSS) (v.22). Kappa agreement analyses were conducted between right-right and left-left deviation and middle cerebral artery (MCA) territory on both 2D and 3D CT scans. A Pearson product moment correlation coefficient was derived to assess covariation between CGAL values and intake NIHSS scores as depicted in FIG. 8. The significance levels for the aforementioned analyses were set at $p<0.05$. Finally, the follow-up MRI data allowed for an identification of true positives and negatives. A receiver operating characteristic (ROC) curve was constructed based on CGAL score and MRI follow up results, from which optimal CGAL values and their respective sensitivities and specificities were determined.

From the initial 519 patients, a total of 103 patients with suspected CVA were included in the final analysis (due to exclusions). Follow up CT and MRI scans were available for 39 and 31 of these patients, respectively. Patient demographic characteristics of the 103 patients are described in Table 1 below:

TABLE 1

| Patient Characteristics | |
|---|---|
| Mean Age | 74 years |
| Male | 74 (72%) |
| Female | 29 (28%) |
| Mean Body Mass Index | 32 |
| Smoker | 62 (64%) |

A CGAL of >0.35 was set as the threshold for the identification of CED. CGAL>0.35 was calculated in 92 patients (89%). CGAL measurements indicated that 45 patient's (44%) ocular deviation was directed rightwards whereas 46 patients (45%) exhibited leftward deviation. These deviations demonstrated strong kappa agreements with clinical MCA territory with rightwards deviation agreements found to be k=0.85 and leftwards deviation agreements found to be k=0.72. A 2D horizontal gaze>11.95° (criteria from step 106) was observed in 78 patients (76%). 2D CED measurements demonstrated that 41 patients (40%) exhibited rightwards deviation and 37 patients (36%) leftwards with deviation-MCA territory agreements found to be k=0.74 and k=0.67 for rightwards and leftwards deviation respectively.

Horizontal gaze deviation was noted in 22 of the 39 CT follow up scans (56%). Additionally, a CGAL value greater than 0.35 was noted in sixteen (42%) of these follow up CT scans. Kappa agreements for deviation direction-MCA infarct territory were k=0.39 for rightwards deviation and k=0.45 for leftwards deviation.

Figure 7:
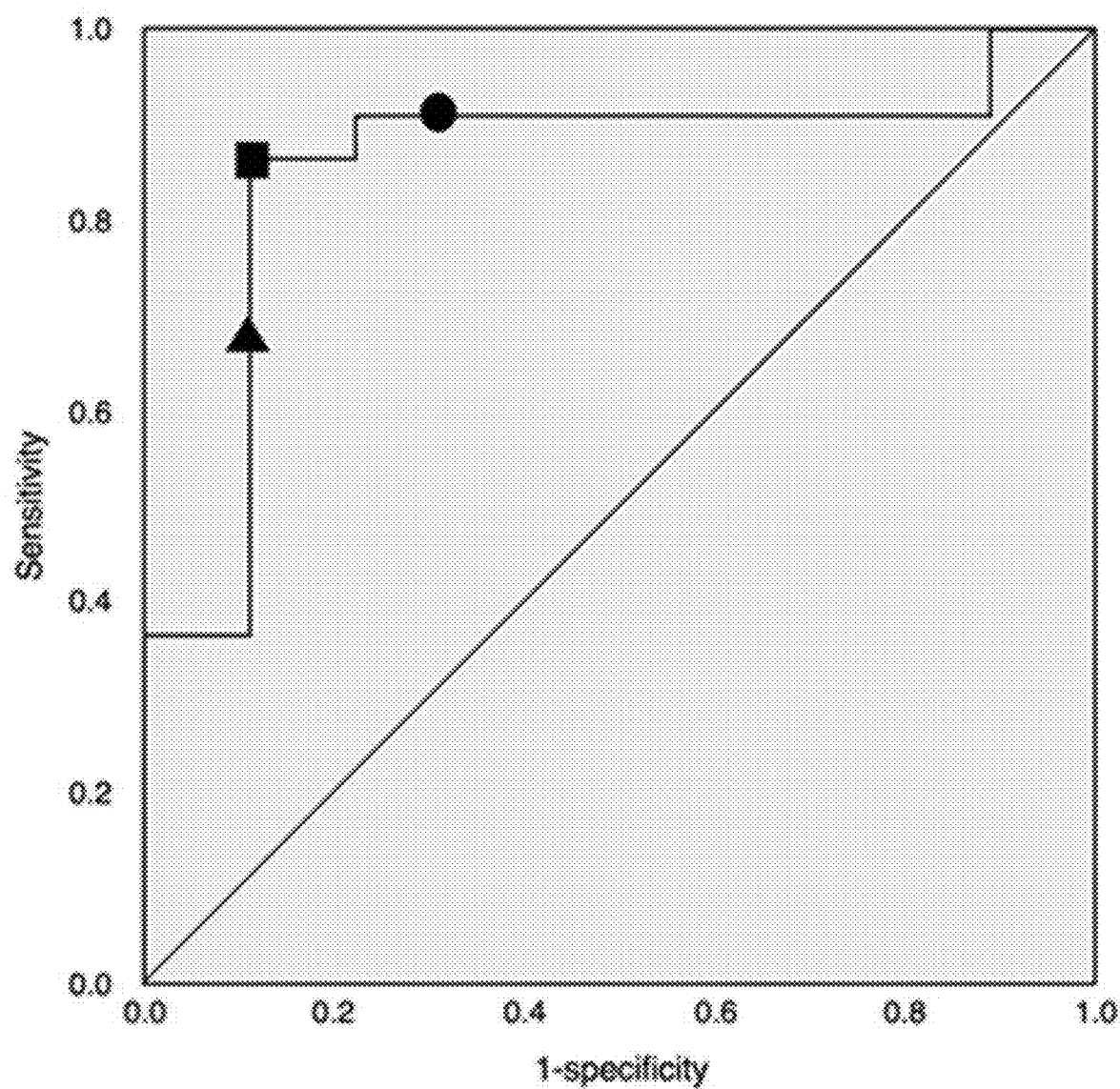
FIG. 7 depicts a ROC curve analysis of the sensitivity and 1-specificity of CGAL in the prediction of AIS produced area under the curve (AUC)=0.85.

Follow up MRI identified a high DWI signal in 22 of the 31 patients for which the data was available. ROC curve analysis of the sensitivity and 1-specificity of CGAL in the pre-diction of AIS produced area under the curve (AUC) =0.85 as depicted in FIG. 7. Three CGAL measurements were evaluated for sensitivity and specificity. CGAL>0.35 was suggested to be an appropriate threshold for the clinical significance of CED through a pilot study, whereas follow up data reported in the present study suggests that a CGAL>0.28 holds a better balance of sensitivity to specificity, and a CGAL>0.25 is an easy value for clinicians to work with. The details of the sensitivity and specificity analysis are reported in Table 2:

TABLE 2

| CGAL Measurement | Sensitivity (True Positives) | Specificity (True Negatives) |
|---|---|---|
| >0.25 | 91% (20) | 66% (6) |
| >0.28 | 86% (19) | 89% (8) |
| >0.35 | 82% (18) | 89% (8) |

CGAL deviation values were found to be strongly and significantly correlated with NIHSS score, as depicted in FIG. 7, for both the left eye (r=0.59, p<0.01) and right eye (r=0.64, p<0.01). When the individual eye CGAL scores were averaged the correlation remained significant (r=0.72, p=0.01). From this data, it was determined that a CGAL range of 0.23-0.27, but more preferably 0.25, can be confidently used as a CGAL diagnostic cut-off This analysis demonstrates the efficacy, utility, and validity of 3D CT image assessments for the presence of CED in the evaluation of AIS. Importantly, a CGAL measurement >0.35, demonstrates a good balance of sensitivity (82%) and specificity (89%). Infarct hemisphere and gaze direction showed strong agreement and, moreover CGAL severity and the NIHSS scale were highly correlated. These findings highlight the validity of CGAL measurements in identifying AIS and quantifying its severity.

The high sensitivity and specificity of a CGAL measurement >0.35 calculated in the current study reflect positively on the use of CGAL measurements in that the presence of both is a hallmark of a strong diagnostic test. Furthermore, the sensitivity rating, in particular, far exceeds that reported for that of 2D CT CED efficacy as well as other standard radiographic signs of AIS such as the detection of hypodensity in greater than 33% of the MCA territory. This suggests that 3D CT image assessments for the presence of CED in suspected AIS patients is an effective diagnostic sign.

Importantly, the analysis of CGAL demonstrates that, in the context of initial neuroimaging scans taken within twenty minutes of hospital admission, a CGAL measurement >0.35 is a highly specific and sensitive indirect sign of AIS. At this early point in stroke code protocol direct radiographic signs of AIS, such as parenchymal changes or infarction, are occasionally undetectable. In the case where an initial CT scan provides unsubstantial evidence for the diagnosis of AIS, an additional follow up CT scan is often performed, which not only subjects the patient to unnecessary radiation, but also consumes valuable time. Indirect CT AIS findings, such as CED diagnosed using CGAL, can guide clinical decision making in the absence of direct findings and allow for progress in patient treatment without the need for a secondary scan. The elimination of this secondary scan is extremely important as nearly 14 billion synapses and 1.9 million neurons are lost for every minute of brain ischemia. Considering the time wasted if imaging is re-performed, it is critical that AIS signs which are apparent in the evaluation of initial CT images, such as CGAL measurements, are available to clinicians.

In applying the findings of this invention there are a few important considerations. First, non-contrast CT is known to have a margin of error of ~1 mm, thereby limiting the spatial resolution when obtaining measurements <1 mm. Moreover, as noted, sensitivity is of greater value then specificity in the context of AIS, therefore in accounting for the limitations of CT spatial resolution it is reasonable to lean on more sensitive thresholds. Finally, a full 3D reconstruction and measurement may be time consuming. Thus, although ROC curve analysis indicated that a CGAL >0.28 exhibits the best balance of sensitivity and specificity, clinicians may save time and reduce the risk of false negatives by considering a rule of thumb wherein an approximate ¼ deviation in the ipsilateral direction is considered a sensitive (91%) ancillary sign for AIS.

Beyond the excellent sensitivity and specificity of a CGAL measurement >0.35, the validity of 3D CT imaging for the assessment of CED in AIS patients is further strengthened by multiple findings of the benefits of CGAL. In concordance with prior investigations of CED in AIS patients, as well as the evaluation of 2D scans used in the present study, there was a high agreement between the direction of deviation noted via 3D CT evaluation and clinical MCA infarct territory. Moreover, the present study identified a strong correlation between CGAL measurements and the NIHSS scale scores (FIG. 7). The fact that the 3D CT assessment of CED is in line with prior 2D CT research and empirically validated stroke scales is a good indication that 3D method has a similar level of validity to the classically used 2D method as a radiographic sign of AIS.

A CGAL >0.35 was found in near equal proportions within both left and right CED gaze direction patients. Although rightward directed gaze has typically thought to be far more common in AIS patients, this analysis casts doubt on this finding. Because deviation is typically ipsilateral to the damaged hemisphere, as it generally was in the present analysis, this finding suggests that CED is not specific to right hemispheric strokes.

In conclusion, a CGAL value >0.28 found in the 3D CT assessment of CED in patients with suspected CVAs is a quick, accurate and useful addition to other radiographic signs. Such a tool can aid in the clinician's decision making processes in the context of otherwise negative or ambiguous CT scan imaging and, therefore, speed up a protocol where time is of the absolute essence.

The invention claimed is:

1. A method for identifying (acute ischemic strokes) AIS by computing a conjugate gaze adjusted length (CGAL), the method comprising:
   a) performing a cross sectional imaging of a brain of a patient;
   b) generating a 3D volume rendered model of the brain;
   c) determining a clipping plane in the 3D volume rendered model by tilting a regular coronal orthogonal 90° plane and fitting the regular coronal orthogonal 90° plane coronal plane to a virtual line connecting the frontal bone to the zygoma in the sagittal plane, wherein, for each eye of the patient, the clipping plane includes a lens of the eye and a globe of the eye;
   d) generating a snapshot using the clipping plane;
   e) measuring a deviation length of each eye in the snapshot;
   f) measuring a globe radius of each eye; and
   g) calculating the CGAL for each eye by dividing the deviation length of each eye by the globe radius of each eye.

2. The method according to claim 1, further comprising: generating a deviation angle for each eye using a four quarter azimuth algorithm.

3. The method according to claim 1, wherein AIS is identified for the patient if CGAL for either eye >0.23.

4. The method according to claim 1, wherein AIS is identified for the patient if CGAL for either eye >0.28.

5. The method according to claim 1, wherein the clipping plane is clipped tangentially to the frontal bone.

6. The method according to claim 5, wherein the clipping plane includes a portion of a roof of an orbit and a zygomatic arch.

7. The method according to claim 1, wherein the 3D volume rendered model of the brain is not generated if a measured 2D horizontal gaze <11.95°.

8. The method according to claim 1, wherein CGAL is determined within 20 minutes of admittance of the patient for suspected AIS.

9. The method according to claim 4, further comprising:
   h) performing a follow up magnetic resonance imaging (MRI) scan of the patient if CGAL >0.28.

* * * * *